United States Patent
Li et al.

(10) Patent No.: US 10,743,926 B2
(45) Date of Patent: Aug. 18, 2020

(54) OSTEO-IMPLANT

(71) Applicant: Industrial Technology Research Institute, Hsinchu (TW)

(72) Inventors: Ming-Jun Li, Yunlin County (TW); Hong-Jen Lai, Hsinchu (TW); Pei-I Tsai, Hsinchu (TW); Fang-Hei Tsau, Kaohsiung (TW); Wei-Chin Huang, Tainan (TW); Yu-Tsung Chiu, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 7 days.

(21) Appl. No.: 16/228,697

(22) Filed: Dec. 20, 2018

(65) Prior Publication Data

US 2020/0197059 A1  Jun. 25, 2020

(51) Int. Cl.
*A61B 17/84*  (2006.01)
*A61B 17/86*  (2006.01)
*A61B 17/72*  (2006.01)

(52) U.S. Cl.
CPC ........ *A61B 17/844* (2013.01); *A61B 17/7258* (2013.01); *A61B 17/86* (2013.01); *A61B 17/869* (2013.01); *A61B 2017/8655* (2013.01)

(58) Field of Classification Search
CPC . A61B 17/72; A61B 17/7208; A61B 17/7233; A61B 17/7258; A61B 17/7266; A61B 17/7275; A61B 17/84; A61B 17/844; A61B 17/86; A61B 17/863; A61B 17/864; A61B 2017/8655; A61B 17/8685; A61B 17/869; A61F 2/4425; A61F 2002/443
See application file for complete search history.

(56) References Cited

U.S. PATENT DOCUMENTS

| | | | |
|---|---|---|---|
| 7,087,055 B2 * | 8/2006 | Lim | A61B 17/025 606/198 |
| 7,727,278 B2 | 6/2010 | Olsen et al. | |
| 7,846,206 B2 * | 12/2010 | Oglaza | A61F 2/4425 623/17.11 |

(Continued)

FOREIGN PATENT DOCUMENTS

| | | |
|---|---|---|
| CN | 104665913 | 6/2015 |
| CN | 105769313 | 7/2016 |

(Continued)

OTHER PUBLICATIONS

"Office Action of Taiwan Counterpart Application," dated Sep. 18, 2019, p. 1-p. 10.

*Primary Examiner* — Larry E Waggle, Jr.
(74) *Attorney, Agent, or Firm* — JCIPRNET (57) ABSTRACT

An osteo-implant including two end portions, at least one middle structure, and a plurality of connection portions is provided. The middle structure is disposed between the two end portions and includes a plurality of middle portions. The middle portions are connected to the two end portions through the connection portions. When the two end portions are moved relatively along an axial direction of the osteo-implant, the two end portions drive the middle portions to push with each other and have displacements along a radial direction of the osteo-implant through the connection portions, such that an outer diameter of the osteo-implant is increased by the middle portions.

18 Claims, 7 Drawing Sheets

(56) References Cited

U.S. PATENT DOCUMENTS

| | | | |
|---|---|---|---|
| 8,579,947 B2 | 11/2013 | Wu | |
| 9,421,048 B2* | 8/2016 | Lee | A61B 17/7208 |
| 9,770,339 B2* | 9/2017 | Greenhalgh | A61B 17/8858 |
| 2015/0018891 A1 | 1/2015 | Culbert | |
| 2015/0272633 A1* | 10/2015 | Suh | A61B 17/7097 |
| | | | 606/323 |
| 2018/0092677 A1 | 4/2018 | Peterson et al. | |
| 2018/0125674 A1* | 5/2018 | Liu | A61F 2/4425 |

FOREIGN PATENT DOCUMENTS

| | | |
|---|---|---|
| TW | 200927064 | 7/2009 |
| TW | 201043188 | 12/2010 |
| TW | I565445 | 1/2017 |

\* cited by examiner

OSTEO-IMPLANT

TECHNICAL FIELD

The disclosure relates to an implant, and more particularly, to an osteo-implant.

DESCRIPTION OF RELATED ART

In the case of medical implants, insufficient stability provided by the implants is the main reason leading to poor or unsuccessful post-surgery recovery most of the time. Taking a general bone screw for example, the bone screw is subjected to the load of daily activities of the human body after being implanted, so the radial dimension of the bone screw is extended when the bone screw is subjected to a compression load in the axial direction as affected by the Poisson's ratio of the material. Nevertheless, the radial dimension of the bone screw shrinks when the bone screw is subjected to a tensile load in the axial direction, and the bone screw may thereby become loose. Therefore, if a bone screw is subjected to multiple loads after being implanted into the human body, stability of the bone screw may be insufficient.

Although the technique of applying extension claws to allow bone screws to achieve radial extension is currently provided, damages caused by the extension claws on the bones may lower the fixation effect generated by the bone screws on soft tissues. In addition, some of the bone screws are now designed to feature a positive Poisson's ratio or a negative Poisson's ratio, so the bone screws may generate radial extension when being subjected to axial compression or may generate radial extension when being subjected to axial tension. Nevertheless, such technique only allows the bone screws to bear a unidirectional load (the axial compression load or the axial tensile load) to generate the radial extension effect, and the bone screws are incapable of generating radial extension when being subjected to both the axial compression load and the axial tensile load. If the position where a bone screw is implanted is subjected to multiple forces, stability of the bone screw may be easily affected. Further, shape-memory alloys are also used nowadays to allow a bone screw to generate radial extension, and the operating mechanism of such technique relies on temperature changes. Nevertheless, temperature differences before and after a bone screw is implanted may be difficult to predict, so it may be difficult to achieve the expected extension effect.

SUMMARY

The disclosure provides an osteo-implant featuring favorable stability after being implanted into an affected part.

An osteo-implant provided by an embodiment of the disclosure includes two end portions, at least one middle structure, and a plurality of connection portions. The middle structure is disposed between the two end portions and includes a plurality of middle portions. The middle portions are connected to the two end portions through the connection portions. When the two end portions are moved relatively along an axial direction of the osteo-implant, the two end portions drive the middle portions to push with each other and have displacements along a radial direction of the osteo-implant through the connection portions, such that an outer diameter of the osteo-implant is increased by the middle portions.

In an embodiment of the disclosure, the middle portions are connected to one of the end portions through one part of the connection portions, and the middle portions are connected to the other end portion through the other part of the connection portions.

In an embodiment of the disclosure, an outer side of each of the end portions has an end portion thread, the middle structure has a middle thread, and the two end portion threads and the middle thread form an outer thread of the osteo-implant.

In an embodiment of the disclosure, a gap is provided between any adjacent two middle portions, and the gap is less than 50% of an outer diameter of each of the middle portions.

In an embodiment of the disclosure, the at least one middle structure has an opening, and the opening is surrounded and formed by the middle portions.

In an embodiment of the disclosure, the opening is a non-round hole.

In an embodiment of the disclosure, the at least one middle structure includes a filling portion, and the filling portion fills the opening.

In an embodiment of the disclosure, the filling portion has another opening.

In an embodiment of the disclosure, the another opening is a non-round hole.

In an embodiment of the disclosure, the opening is polygon-shaped, each of the middle portions has a tip, and the tips of the middle portions form a plurality of vertexes of the opening.

In an embodiment of the disclosure, each of the connection portions is helix-shaped.

In an embodiment of the disclosure, the two connection portions connected to opposite two sides of each of the middle portions are forward helixes or reverse helixes.

In an embodiment of the disclosure, when the two end portions are moved relatively along the axial direction of the osteo-implant, each of the middle portions is moved, and a rotation axis of each of the middle portions is parallel to the axial direction of the osteo-implant.

In an embodiment of the disclosure, when the two end portions are moved away from each other along the axial direction of the osteo-implant, each of the middle portions rotates in a first rotation direction, when the two end portions are moved close to each other along the axial direction of the osteo-implant, each of the middle portions rotates in a second rotation direction, and the first rotation direction is opposite to the second rotation direction.

In an embodiment of the disclosure, an outer diameter of each of the connection portions is 0.4 to 15 millimeters.

In an embodiment of the disclosure, a length of each of the connection portions along the axial direction of the osteo-implant is 10 to 50 millimeters.

In an embodiment of the disclosure, each of the middle portions is connected to one end portion through at least two of the connection portions.

In an embodiment of the disclosure, a length of the connection portions along the axial direction of the osteo-implant accounts for 10 to 80% of a length of the osteo-implant.

In an embodiment of the disclosure, a number of the at least one middle structure is plural, and the middle structures are connected between the two end portions in sequence through the connection portions.

In an embodiment of the disclosure, a number of the connection portions is in multiples of a number of the middle portions.

To sum up, in the osteo-implant provided by the embodiments of the disclosure, movements of the two end portions along the axial direction may drive the middle portions to push with each other. Therefore, regardless of an axial compression load or an axial tensile load applied to the two end portions, the osteo-implant may provide the effect of radial extension through radial displacements generated by the middle portions when pushing with each other, so that the osteo-implant may provide favorable stability after being implanted into an affected part.

To make the aforementioned more comprehensible, several embodiments accompanied with drawings are described in detail as follows.

DESCRIPTION OF THE EMBODIMENTS

Figure 1:
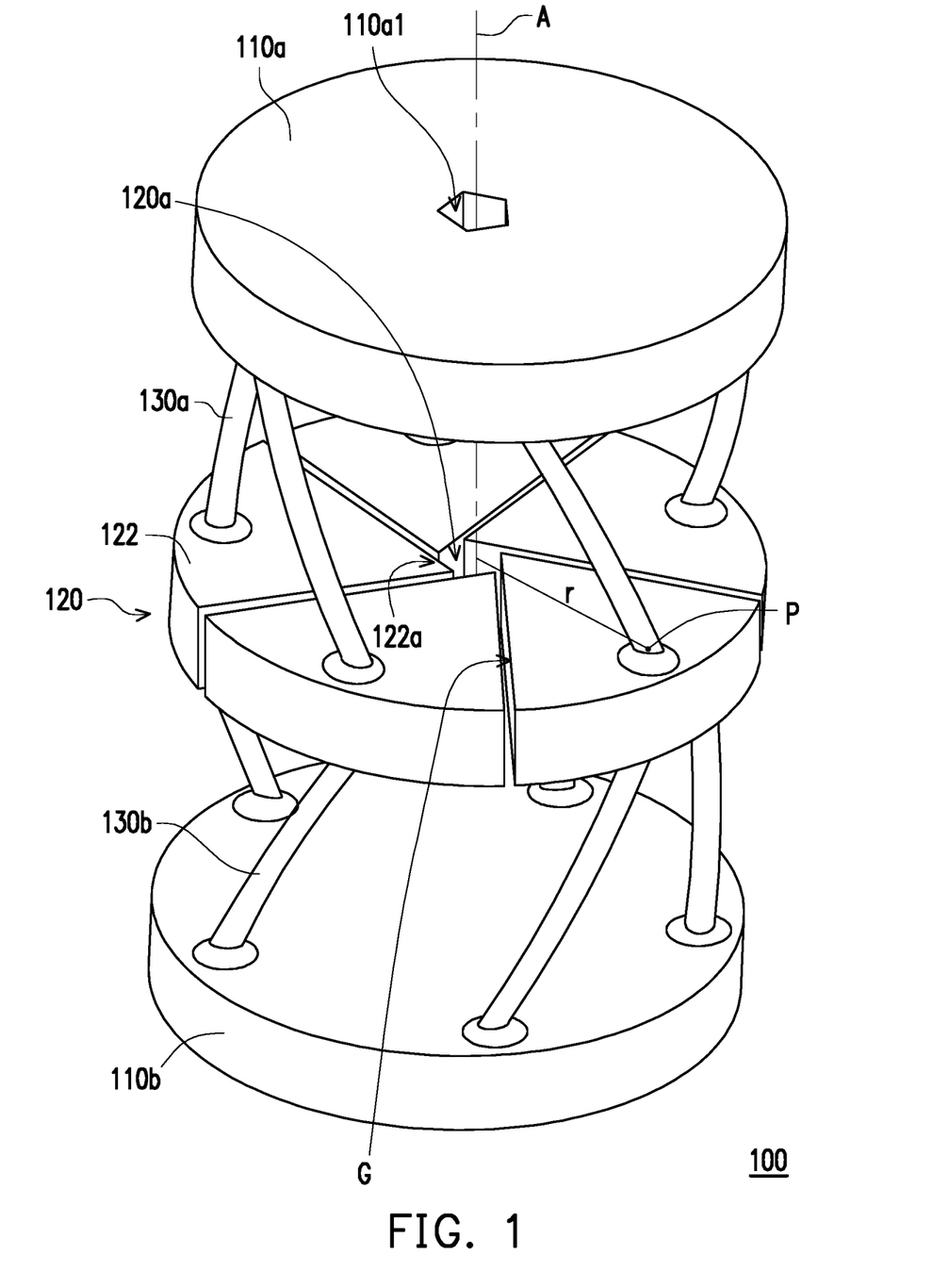
FIG. 1 is a three-dimensional view of part of a structure of an osteo-implant according to an embodiment of the disclosure.

FIG. 1 is a three-dimensional view of part of a structure of an osteo-implant according to an embodiment of the disclosure. With reference to FIG. 1, an osteo-implant 100 of this embodiment is, for example, a bone screw, and an external thread structure of the bone screw is not depicted in this embodiment for the sake of clearness of the drawing. The osteo-implant 100 includes two end portions (marked as an end portion 110a and an end portion 110b), a middle structure 120, and a plurality of connection portions (marked as a plurality of connection portions 130a and a plurality of connection portions 130b). The middle structure 120 is disposed between the two end portions 110a and 110b and includes a plurality of middle portions 122. The connection portions 130a and 130b are, for example, helical structures having appropriate pitches, which is not limited by the disclosure in this regard. The middle portions 122 are connected to the end portion 110a through the connection portions 130a and are connected to the end portion 110b through the connection portions 130b.

When the two end portions 110a and 110b are moved relatively along an axial direction A of the osteo-implant 100, the two end portions 110a and 110b drive the middle portions 122 to push with each other and have displacements along a radial direction of the osteo-implant 100 through the connection portions 130a and 130b, such that an outer diameter of the osteo-implant 100 is increased by the middle portions 122. The radial direction is perpendicular to the axial direction A.

Figure 2A:
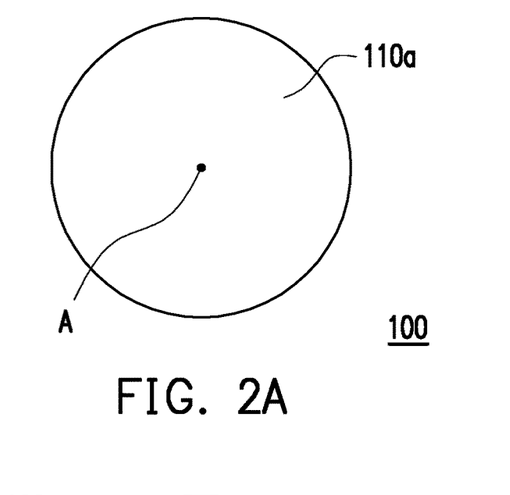
FIG. 2A to FIG. 2C illustrate radial displacements generated by middle portions of FIG. 1.
Figure 2B:
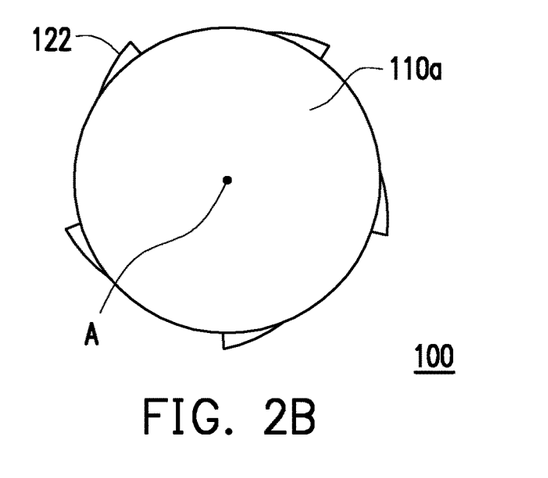
Figure 2C:
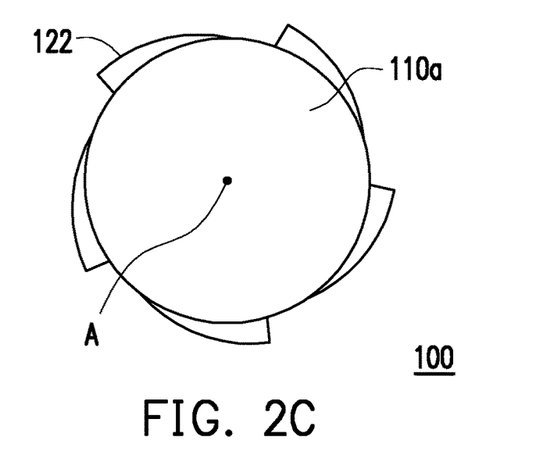

FIG. 2A to FIG. 2C illustrate radial displacements generated by the middle portions of FIG. 1, and the osteo-implant 100 is observed based on a viewing angle along the axial direction A. To be specific, the osteo-implant 100 is in the state shown in FIG. 1 and FIG. 2A when not being subjected to an axial load. When the osteo-implant 100 is subjected to a tensile load so that the two end portions 110a and 110b are moved away from each other along the axial direction A, each of the middle portions 122 rotates in a first rotation direction (the counter-clockwise direction shown in FIG. 2A to FIG. 2C), pushes with each other, and protrudes along the radial direction as shown in FIG. 2B, and a rotation axis thereof, for example, is parallel to but does not overlap the axial direction A. Similarly, when the osteo-implant 100 is not subjected to an axial compression load so that the two end portions 110a and 110b are moved closer to each other along the axial direction A, each of the middle portions 122 rotates in a second rotation direction (the clockwise direction shown in FIG. 2A to FIG. 2C), pushes with each other, protrudes along the radial direction as shown in FIG. 2C, and the rotation axis thereof, for example, is parallel to but does not overlap the axial direction A.

As described above, movements of the two end portions 110a and 110b along the axial direction A may drive the middle portions 122 to push with each other. Hence, regardless of the axial compression load or the axial tensile load applied to the two end portions 110a and 110b, the osteo-implant 100 may provide the effect of radial extension through radial displacements generated by the middle portions 122 when pushing with each other, so that the osteo-implant 100 may provide favorable stability after being implanted into an affected part.

Further, in this embodiment, a gap G is provided between any adjacent two middle portions 122. If the gap G is excessively large, when the middle portions 122 rotate, only displacements instead of radial displacements extending externally shown in FIG. 2B and FIG. 2C are generated at the gap G, so a smaller gap G is preferred. Accordingly, the gap G of this embodiment is, for example, less than 50% of the outer diameter of each of the middle portions 122, so the middle portions 122 may certainly push with each other when being moved, and the effect of radial displacements extending externally is thereby generated. In other embodiments, the gap G may be less than 30%, 20%, or 10% of the outer diameter of each of the middle portions 122. Certainly, if the gap G may be formed to be even smaller through the manufacturing technology, the gap G may be less than 5%, 2%, 1%, 0.5%, or 0.1% of the outer diameter of each of the middle portions 122. To be specific, the gap G may be any appropriate value less than or equal to 0.1 millimeter, 0.2 millimeter, or 0.5 millimeter, which is not limited by the disclosure in this regard.

In this embodiment, the middle structure 120 has an opening 120a, and the opening 120a is surrounded and formed by the middle portions 122. The end portion 110a has another opening 110a1 corresponding to the opening 120a, and the opening 120a and the opening 110a1 are both non-round holes. Accordingly, a user may insert a tool into the opening 120a and the opening 110a1 and drives the osteo-implant 100 to rotate through the tool to be locked to the affected part. For instance, the opening 120a and the opening 110a1 of this embodiment are both polygon-shaped so as to correspond to a tool having a polygonal cross-section. Further, each of the middle portions 122 has a tip 122a as shown in FIG. 1, and the tips 122a of the middle portions 122 form a plurality of vertexes of the opening 120a. Since a number of the middle portions 122 in this embodiment is five, the opening 120a surrounded and formed by the middle portions 122 through the foregoing manner is shaped as a pentagon. In other embodiments, the number of the middle portions 122 may be other appropriate numbers and opening 120a and the opening 110a1 may be shaped as other appropriate shapes, or the opening 120a may not have to be formed, which is not limited by the disclosure in this regard. Examples are described through drawings as follows.

Figure 3:
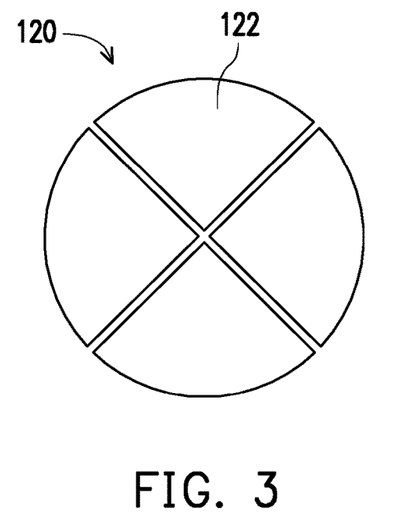
FIG. 3 is a schematic view of a middle structure according to another embodiment of the disclosure.
Figure 4:
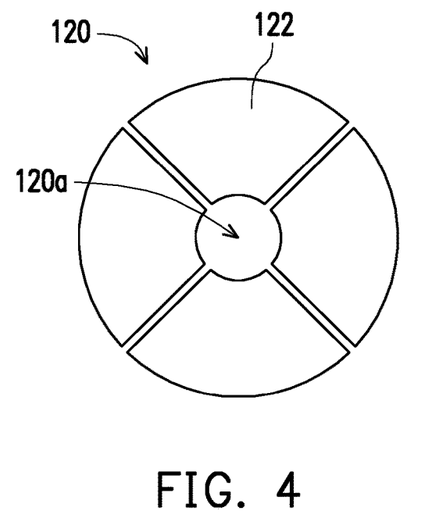
FIG. 4 is a schematic view of a middle structure according to another embodiment of the disclosure.
Figure 5:
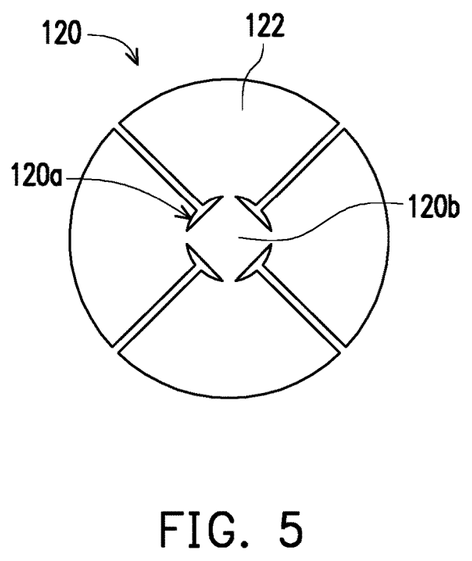
FIG. 5 is a schematic view of a middle structure according to another embodiment of the disclosure.
Figure 6:
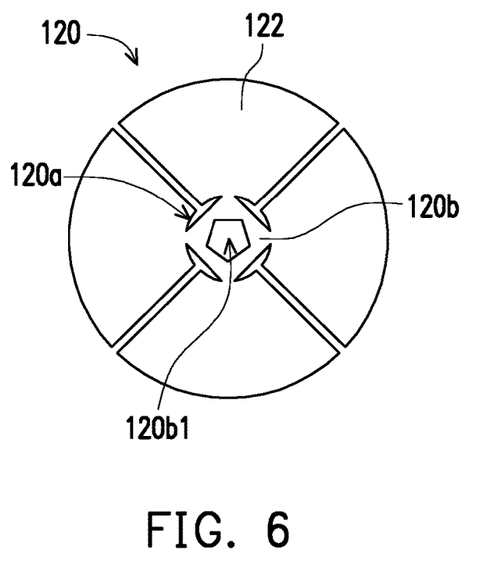
FIG. 6 is a schematic view of a middle structure according to another embodiment of the disclosure.

FIG. 3 is a schematic view of a middle structure according to another embodiment of the disclosure, and the difference between the embodiment shown in FIG. 3 and the embodiment shown in FIG. 1 is that the number of the middle portions 122 of the middle structure 120 of FIG. 3 is four, and the middle structure 120 does not have the opening 120a shown in FIG. 1. FIG. 4 is a schematic view of a middle structure according to another embodiment of the disclosure, and the difference between the embodiment shown in FIG. 4 and the embodiment shown in FIG. 3 is that the middle structure 120 of FIG. 4 has a round opening 120a. FIG. 5 is a schematic view of a middle structure according to another embodiment of the disclosure, and the difference between the embodiment shown in FIG. 5 and the embodiment shown in FIG. 4 is that the middle structure 120 of FIG. 4 includes a filling portion 120b, and the filling portion 120b fills the opening 120a to prevent the opening 120a and the gap G from providing excessive inwardly-moving displacement space to the middle portions 122 so that the middle portions 122 may not be able to generate sufficient radial extension displacements. FIG. 6 is a schematic view of a middle structure according to another embodiment of the disclosure, and the difference between the embodiment shown in FIG. 6 and the embodiment shown in FIG. 5 is that the filling portion 120b of FIG. 6 has an opening 120b1, and the opening 120b1 is a non-round hole (depicted as a pentagon) to allow the user to use a tool to insert into the opening 120b1 and drive the osteo-implant 100 to rotate through the tool to be fixed to the affected part.

Figure 7:
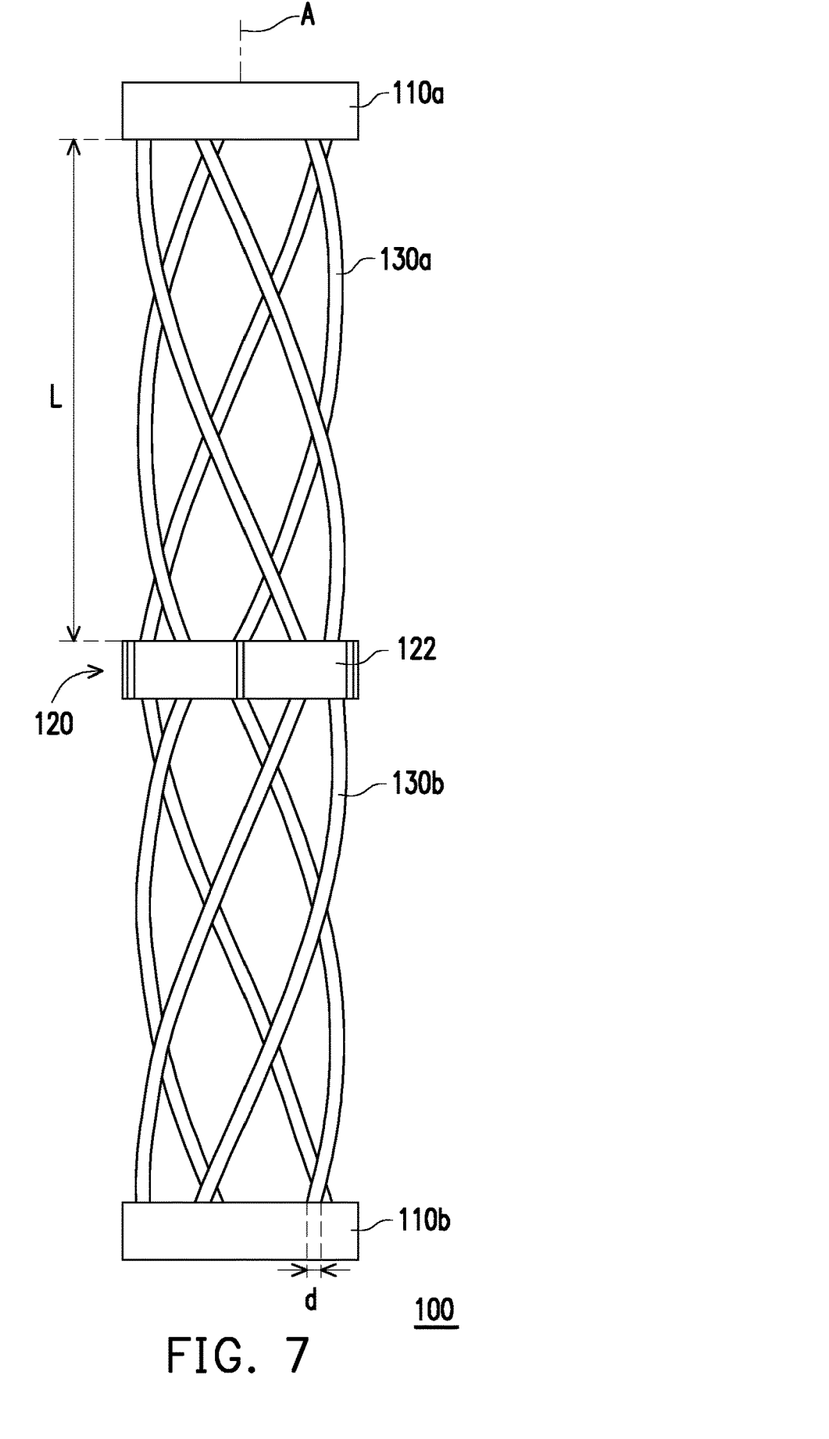
FIG. 7 is a schematic side view of the osteo-implant of FIG. 1.
Figure 8:
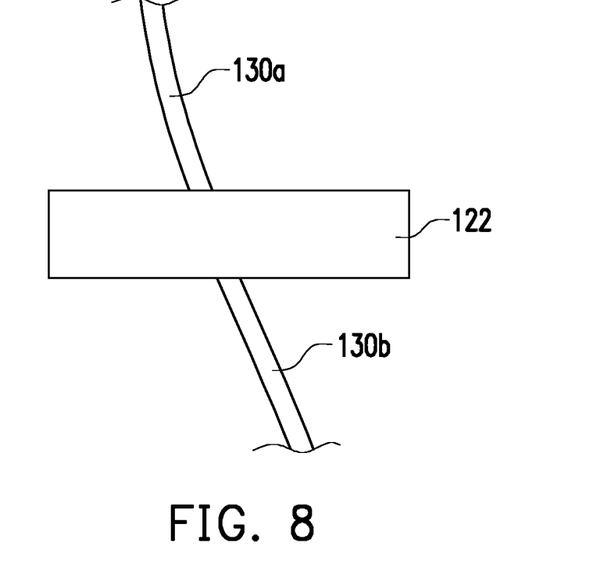
FIG. 8 is a schematic side view of part of members of the osteo-implant according to another embodiment of the disclosure.

FIG. 7 is a schematic side view of the osteo-implant of FIG. 1. From FIG. 7, it can be clearly seen that the two connection portions 130a and 130b connected to opposite two sides of each of the middle portions 122 are reverse helixes. Accordingly, when the two end portions 110a and 110b are moved relatively along the axial direction A, directions of transverse pushing forces (or pulling forces) applied by the two connection portions 130a and 130b on the corresponding middle portion 122 are identical, so the forces are added up instead of counteracting on each other. Nevertheless, the disclosure is not limited thereto, and FIG. 8 is a schematic side view of part of members of the osteo-implant according to another embodiment of the disclosure, where the corresponding two connection portions 130a and 130b may also be forward helixes as shown in FIG. 8.

Description of design parameters is provided as follows by taking the osteo-implant 100 for example.

As shown in FIG. 7, an outer diameter d of each of the connection portions 130a and 130b is, for example, 0.4 to 15 millimeters, and in response to that the outer diameter d of each of the connection portions 130a and 130b increases, overall structural strength of the osteo-implant 100 increases. In this embodiment, the outer diameter d of each of the connection portions 130a and 130b is, for example, 2 to 25% of the outer diameter of the osteo-implant 100. Besides, each of the connection portions 130a and 130b may be a structure having unequal outer diameters and having at least a first outer diameter and a second outer diameter distinct from each other, and the first diameter is, for example, 0.5 to 1.5 times greater than the second outer diameter.

As shown in FIG. 7, a length L of each of the connection portions 130a and 130b along the axial direction A of the osteo-implant 100 is, for example, 10 to 50 millimeters, and in response to that the length L of each of the connection portions 130a and 130b increases, each of the connection portions 130a and 130b may be deformed and extended in the radial direction to a greater extent. In this embodiment, a length of the connection portions 130a and 130b in the axial direction A of the osteo-implant 100 accounts for, for example, 10 to 80% of a length of the osteo-implant 100.

As shown in FIG. 1, an end point P of each of the connection portions 130a and 130b is connected to the corresponding middle portion 122, and a distance r between the end point P and a central axis (i.e., the axial direction A) of the osteo-implant 100 is 2 to 6 millimeters or is 0.15 to 0.7 times greater than the outer diameter of the osteo-implant 100. In response to that the distance r between the end point P and the central axis (i.e., the axial direction A) of the osteo-implant 100 decreases, the overall structural strength of the osteo-implant 100 increases.

Figure 9:
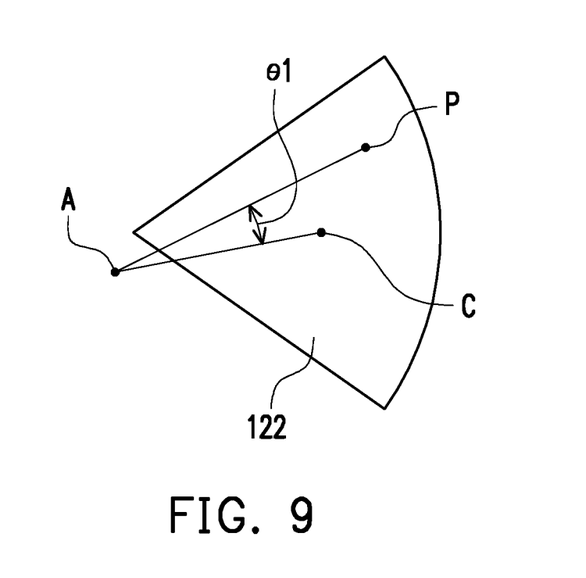
FIG. 9 is a schematic top view of part of the members of the osteo-implant of FIG. 1.

FIG. 9 is a schematic top view of part of the members of the osteo-implant of FIG. 1. As shown in FIG. 9, the end point P of each of the connection portions 130a and 130b (marked in FIG. 1) is connected to the corresponding middle portion 122, a first connection line is provided between each of the end point P and the central axis (i.e., the axial direction A) of the osteo-implant 100 (marked in FIG. 1), a second connection line is provided between a geometric center C of each of the connection portions and the central axis A of the osteo-implant 100, and an included angle θ1 between the first connection line and the second connection line is 0 to 4 degrees.

Figure 10:
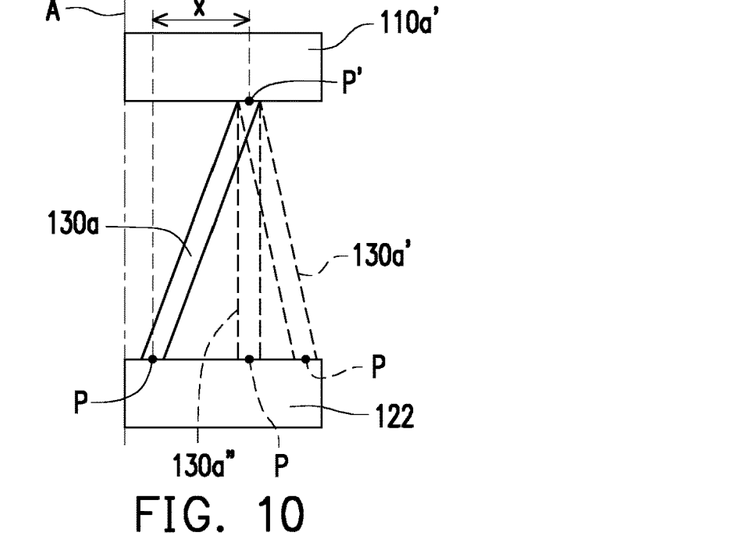
FIG. 10 is a schematic side view of part of the members of the osteo-implant of FIG. 1.

FIG. 10 is a schematic side view of part of the members of the osteo-implant of FIG. 1. As shown in FIG. 10, the end point P of each of the connection portions (the connection portion 130a is taken as an example in FIG. 10) is connected to the corresponding middle portion 122, another end point P' of each of the connection portions (the connection portion 130a is taken as an example in FIG. 10) is connected to one end portion (the connection portion 110a is taken as an example in FIG. 10), and a distance x between the end point P and the end point P' in the radial direction of the osteo-implant 100 is 0 to 0.4 millimeter. The end point P of the connection portion 130a is depicted to be located at a radially inner side with respect to the end point P' in FIG. 10, but the disclosure is not limited thereto, so the end point P may be located at a radially outer side with respect to the end point P' such as a connection portion 130a' illustrated by dotted lines shown in FIG. 10, or the end point P and the end point P' show no relative offset in the radial direction such as a connection portion 130a" illustrated by dotted lines shown in FIG. 10.

In the foregoing embodiments, each of the middle portions 122 is connected to the end portion 110a through one connection portion 130a, and each of the middle portions 122 is connected to the end portion 110b through one connection portion 130b. That is, a number of the middle portions 122 is equal to a number of the connection portions 130a and is equal to a number of the connection portions 130b. Nevertheless, the disclosure is not limited thereto, so each of the middle portions 122 may be connected to the end portion 110a through multiple connection portions 130a, and each of the middle portions 122 may be connected to the end portion 110b through multiple connection portions 130b, so as to enhance the overall structural strength of the osteo-implant 100. That is, the number of the connection portions 130a is in multiples of the number of the middle portions 122, and the number of the connection portions 130b is in multiples of the number of the middle portions 122.

In addition, in the foregoing embodiments, a number of the middle structure 120 is one. Nevertheless, the disclosure is not limited thereto, so the number of the middle structure 120 can be multiple, and the multiple middle structures 120 are connected between the two end portions 110a and 110b in sequence through the multiple connection portions.

Description of design parameters is provided as follows by taking an osteo-implant of other embodiments for example.

Figure 11:
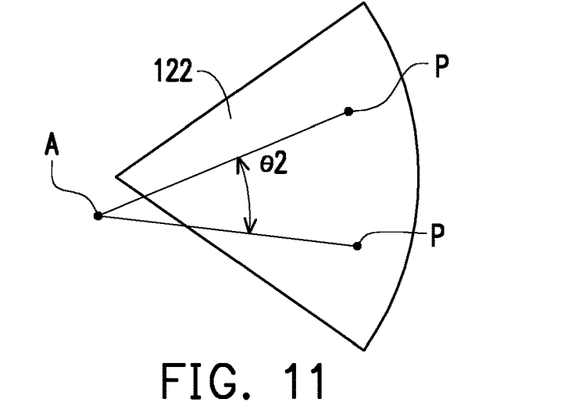
FIG. 11 is a schematic top view of part of the members of the osteo-implant according to another embodiment of the disclosure.

FIG. 11 is a schematic top view of part of the members of the osteo-implant according to another embodiment of the disclosure. In the embodiment shown in FIG. 11, each of the middle portions 122 is connected to the end portion (such as the end portion 110a or the end portion 110b of the foregoing embodiments) through at least two connection portions (such as the connection portions 130a or the connection portions 130b of the foregoing embodiments), the end point P of each of the connection portions is connected to the corresponding middle portion, a connection line is provided between each of the end points P and the central axis (i.e., the axial direction A), and an included angle θ2 between two connection lines corresponding to each of the middle portions is 0 to 30 degrees.

Figure 12:
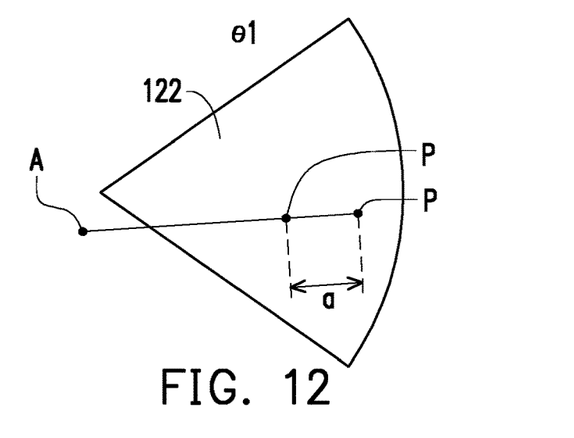
FIG. 12 is a schematic top view of part of the members of the osteo-implant according to another embodiment of the disclosure.

FIG. 12 is a schematic top view of part of the members of the osteo-implant according to another embodiment of the disclosure. In the embodiment shown in FIG. 12, each of the middle portions 122 is connected to the end portion (such as the end portion 110a or the end portion 110b of the foregoing embodiments) through at least two connection portions (such as the connection portions 130a or the connection portions 130b of the foregoing embodiments), the end point P of each of the connection portions is connected to the corresponding middle portion, a connection line corresponding to the two end points P of each of the middle portions 122 passes through the central axis (i.e., the axial direction A), and a distance a between the two end points P is, for example, 2 to 2.8 millimeters.

Figure 13:
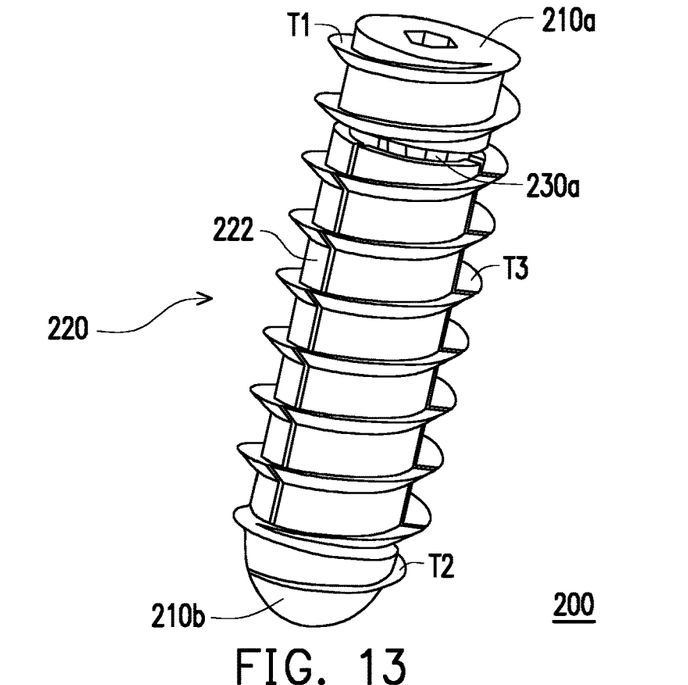
FIG. 13 is a three-dimensional view of an osteo-implant according to another embodiment of the disclosure.
Figure 14:
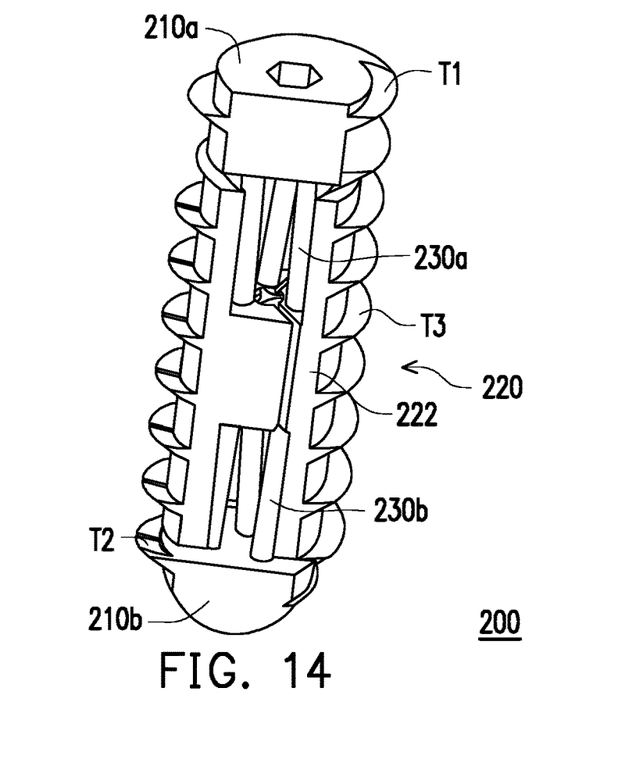
FIG. 14 is a three-dimensional view of a local structure of the osteo-implant of FIG. 13.

FIG. 13 is a three-dimensional view of an osteo-implant according to another embodiment of the disclosure. FIG. 14 is a three-dimensional view of a local structure of the osteo-implant of FIG. 13. In an osteo-implant 200 of FIG. 13 and FIG. 14, an end portion 210a, an end portion 210b, a middle structure 220, middle portions 222, connection portions 230a, and connection portions 230b are disposed and function in a manner similar to that of how the end portion 110a, the end portion 110b, the middle structure 120, the middle portions 122, the connection portions 130a, and the connection portions 130b are disposed and function, and similar description is thus omitted herein. FIG. 13 and FIG. 14 illustrate an external thread structure of a bone screw. To be specific, as shown in FIG. 13 and FIG. 14, an outer side of the end portion 210a has an end portion thread T1, an outer side of the end portion 210b has an end portion thread T2, the middle structure 220 has a middle thread T3, and the two end portion threads T1 and T2 and the middle thread T3 form an outer thread of the osteo-implant 200 configured to be fixed to an affected part.

The end portions, the middle structure, and the connection portions in the foregoing embodiments may be manufactured through three-dimensional printing; nevertheless, the disclosure is not limited thereto, so the end portions, the middle structure, and the connection portions may be manufactured or assembled through other appropriate manners.

Although the embodiments are already disclosed as above, these embodiments should not be construed as limitations on the scope of the disclosure. It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. An osteo-implant, comprising:
   two end portions;
   at least one middle structure, disposed between the two end portions and comprising a plurality of middle portions; and
   a plurality of connection portions, the plurality of middle portions being connected to the two end portions through the plurality of connection portions, wherein the two end portions drive the plurality of middle portions to push with each other and have displacements along a radial direction of the osteo-implant through the plurality of connection portions when the two end portions are moved relatively along an axial direction of the osteo-implant such that an outer diameter of the osteo-implant is increased by the plurality of middle portions, wherein
   a rotation axis of each of the middle portions is parallel to the axial direction of the osteo-implant when the two end portions are moved relatively along the axial direction of the osteo-implant to drive each of the middle portions to rotate relatively to the end portions along the rotation axis.

2. The osteo-implant as claimed in claim 1, wherein the plurality of middle portions are connected to one of the end portions through one part of the plurality of connection portions, and the plurality of middle portions are connected to the other end portion through another part of the plurality of connection portions.

3. The osteo-implant as claimed in claim 1, wherein an outer side of each of the end portions has an end portion thread, the at least one middle structure has a middle thread, and the two end portion threads and the middle thread form an outer thread of the osteo-implant.

4. The osteo-implant as claimed in claim 1, wherein a gap is provided between any adjacent two middle portions, and the gap is less than 50% of an outer diameter of each of the middle portions.

5. The osteo-implant as claimed in claim 1, wherein the at least one middle structure has an opening, and the opening is surrounded and formed by the plurality of middle portions.

6. The osteo-implant as claimed in claim 5, wherein the opening is a non-round hole.

7. The osteo-implant as claimed in claim 5, wherein the at least one middle structure comprises a filling portion, and the filling portion fills the opening.

8. The osteo-implant as claimed in claim 7, wherein the filling portion has another opening.

9. The osteo-implant as claimed in claim 8, wherein the another opening is a non-round hole.

10. The osteo-implant as claimed in claim 5, wherein the opening is polygon-shaped, each of the middle portions has a tip, and the plurality of tips of the plurality of middle portions form a plurality of vertexes of the opening.

11. The osteo-implant as claimed in claim 1, wherein each of the connection portions is helix-shaped.

12. The osteo-implant as claimed in claim 11, wherein two of the connection portions connected to opposite two sides of each of the middle portions are forward helixes or reverse helixes.

13. The osteo-implant as claimed in claim 1, wherein each of the middle portions rotates in a first rotation direction when the two end portions are moved away from each other along the axial direction of the osteo-implant, each of the middle portions rotates in a second rotation direction when the two end portions are moved close to each other along the axial direction of the osteo-implant, and the first rotation direction is opposite to the second rotation direction.

14. The osteo-implant as claimed in claim 1, wherein an outer diameter of each of the connection portions is 0.4 to 15 millimeters.

15. The osteo-implant as claimed in claim 1, wherein a length of each of the connection portions along the axial direction of the osteo-implant is 10 to 50 millimeters.

16. The osteo-implant as claimed in claim 1, wherein each of the middle portions is connected to one end portion through at least two of the connection portions.

17. The osteo-implant as claimed in claim 1, wherein a length of the connection portions along the axial direction of the osteo-implant accounts for 10 to 80% of a length of the osteo-implant.

18. The osteo-implant as claimed in claim 1, wherein a number of the plurality of connection portions is in multiples of a number of the plurality of middle portions.

* * * * *